(12) United States Patent
Recoules-Arche et al.

(10) Patent No.: US 7,682,394 B2
(45) Date of Patent: Mar. 23, 2010

(54) METHOD FOR REPAIR OF A SPINE AND INTERVERTEBRAL IMPLANT

(75) Inventors: Didier Recoules-Arche, Sainte-Adresse (FR); Robert Velez, Châteauroux (FR); Robert Lange, Paris (FR)

(73) Assignee: Co-Ligne AG, Zurich (CH)

( * ) Notice: Subject to any disclaimer, the term of this patent is extended or adjusted under 35 U.S.C. 154(b) by 804 days.

(21) Appl. No.: 11/448,992

(22) Filed: Jun. 8, 2006

(65) Prior Publication Data
US 2007/0016298 A1    Jan. 18, 2007

(51) Int. Cl.
*A61F 2/44* (2006.01)
(52) U.S. Cl. .................. 623/17.11; 623/17.16
(58) Field of Classification Search ... 623/17.11–17.16, 623/908; *A61F 2/44*
See application file for complete search history.

(56) References Cited

U.S. PATENT DOCUMENTS

| | | | |
|---|---|---|---|
| 5,885,292 A * | 3/1999 | Moskovitz et al. | 606/79 |
| 6,251,140 B1 | 6/2001 | Marino et al. | |
| 6,613,089 B1 | 9/2003 | Estes et al. | |
| 2004/0186572 A1 * | 9/2004 | Lange et al. | 623/17.11 |
| 2005/0154389 A1 * | 7/2005 | Selover et al. | 606/61 |
| 2005/0177240 A1 * | 8/2005 | Blain | 623/17.15 |

FOREIGN PATENT DOCUMENTS

| | | |
|---|---|---|
| EP | 1 430 858 A | 6/2004 |
| WO | WO-95/08306 A | 3/1995 |

OTHER PUBLICATIONS

Wiltse, LL and CW Spencer. New Uses and Refinements of the Paraspinal Approach. Spine, vol. 13, No. 6 (Jun. 13, 1988), pp. 696-706.*
Wiltse, LL; Spencer CW: New Uses and Refinements of the Paraspinal Approach. Spine 13:6, 1988.*

* cited by examiner

*Primary Examiner*—Eduardo C Robert
*Assistant Examiner*—Lynnsy Schneider
(74) *Attorney, Agent, or Firm*—Browdy & Neimark, PLLC

(57) ABSTRACT

Repair of a spine from a posterior approach especially for locating an implant between a lower and upper human vertebra includes making an incision in the skin lateral to the midline, making an incision through the Erector Spinae Aponeurosis (ESA) following the ELIF groove, separating the ESA from the Longissimus Thoracis Pars Lumborum (LTPL), atraumatic separating the Multifidus from the LTPL using the interfascial boundary between the Multifidus and the LTPL, and creating a surgical plane having an angle of 20°-60°.

16 Claims, 16 Drawing Sheets

METHOD FOR REPAIR OF A SPINE AND INTERVERTEBRAL IMPLANT

BACKGROUND OF THE INVENTION

The invention relates to a method for repair of a spine from a posterior approach especially for locating an implant between a lower and upper human vertebra. The invention further relates to an intervertebral implant and especially an implant for fusing together adjoining vertebrae bodies.

Since its earliest history, surgery has been an imperfect compromise between the severity of the disease, the goal to cure, and the damage inflicted by the treatment. Spinal fusion surgery with implants is no different. The spine lies deep within the body. It is adjacent to vital structures that are easily damaged. To reach the spine and the pathology to be treated, many bodily structures are often disrupted or destroyed. Supporting bone of the vertebral column must at times be resected and stabilizing ligaments removed. Vessels providing blood supply are oftentimes cut and nerves can be severed.

For certain patients, a lumbar spinal fusion procedure is chosen for treatment, with the combined goals to decompress the painful nerves, to correct a deformity, to immobilize a painfully moving vertebral segment, and to hold it stable in a desired position while the motion segment fuses or grows into a bridge of bone.

To perform a lumber spinal fusion procedure, the surgeon first decides how to approach the spine, how to reach the pathology and how to build a biomechanical fusion construct, which can be composed of inter vertebral cages with or without pedicle fixation. The prior art often uses a midline posterior approach. This requires the surgeon to dissect the posterior lumbar multifidus muscle at a given level, from the spine's posterior elements and to expose the facet joint and lamina. For access, the surgeon must many times dissect levels above and below the level to be treated to enable the surgeon to decompress bone where needed and to enter the spinal canal in order to insert his cages. Dissection of the multifidus from the posterior elements is also the most commonly used method to give the surgeon access to the pedicles for the insertion of the pedicle screws when these are required. In the weeks following surgery, such dissection leads to atrophy and perhaps in itself, a source of additional pain.

Furthermore, at each segment the medial branch of the dorsal ramus, with its accompanying vascular supply, together called the neurovascular bundle, passes across the lamina to supply specific fascicles of the multifidus at each level. The midline surgical approach for a single fusion level typically disrupts the multifidus from the posterior elements of several vertebrae, two vertebrae of the motion segment to be fused, and at least one level above and one below. This destroys the medial branch of the dorsal ramus and its accompanying vascular supply at the level of fusion, as well as one level above and below. This is yet another way to destroy muscle function because a muscle deprived of its neural and vascular supply tends to atrophy. Over the years that follow surgery, this degeneration of the multifidus, transfers its normal multi level functions to other surrounding muscles not designed for the role normally performed by the multifidus, overworking these other muscles and becoming probably a new source of pain and dysfunction. All spinal surgery and constructs that use the midline posterior surgical approach and its consequent resection of the multifidus, share this problem. In creating morbidity at the segment to be fused, it compromises function at levels above and below, which can effect the entire spine and the patient's wellbeing over the years to come.

In order to avoid the posterior midline approach's damage to the posterior muscles, ligaments, vessels and nerves, some surgeons approach the spine from the abdomen and build a fusion construct placing inter-vertebral body cages from the anterior approach. This technique is called the Anterior Lumbar Interbody Fusion or ALIF and gives the surgeon the ability to achieve segmental lordosis which corrects spinal balance. The ALIF cages provide optimal anterior spinal column support, and places copious bone graft against the cleaned vertebral bony endplates of the vertebral bodies to be fused. The ALIF, when used alone without pedicle fixation, does not disrupt the posterior back muscles, nor does cage placement require decompression or trauma of the posterior structures of the spine.

However, the anterior approach has limitations and dangers of its own. Spinal canal stenosis, requiring significant boney decompression within the spinal canal for treatment, cannot be achieved from the anterior approach. Isthmic sponylolysthesis, where a vertebra slips anteriorly in relation to the one below because of a defect in the pars interarticularis prevent the facets joints from performing their normal breaking function, requires stabilizing in addition to the cages in order to compensate for the deficient facet joints. For ALIF patients, pedicle fixation that replaces the role of facets must be added from a separate posterior approach that disrupts the muscles. Therefore many cases of isthmic sponylolysthesis cannot be treated by the anterior approach, unless stabilization is added such as posterior pedicle fixation. This from the posterior midline, eliminates the ALIF's advantage of saving the muscles. From the ALIF approach, it is possible to disrupt certain neural structures, notably the Sympathetic Trunk which in male patients control function of the sexual organs and can cause retrograde ejaculation, a known complication of the anterior approach. Furthermore, within the community of surgeons who treat spinal disorders, not all are trained to perform abdominal surgery alone or to manage the life threatening blood loss due to injury of the major vessels located in the path to the anterior spinal column. Thus, many spine surgeons prefer to place their inter-vertebral-body cages from the posterior approach, regardless of the pathology, most often in a surgical procedure called Posterior Lumbar Interbody Fusion or PLIF, which in recent years, is most often associated with pedicle fixation.

Over the last twenty years, artificial discs have been developed in the hopes to restore motion and therefore function to a diseased spinal motion segment. Also referred to as spinal arthroplasty, the goal of these implants is to create an artificial joint. Here lies the limitation of current technology. A spinal motion segment consists of a three joint complex, consisting of two facet joints and the disc. In their present form, only the disc is replaced and most diseased motion segments have degeneration in all three joints as advanced disc disease often presents advanced facet hypertrophy and stenosis. The painless function of the artificial disc requires healthy function of the facets. Artificial facets could be considered, but a means to replace them would have to be found that does not destroy surrounding muscles required for the motion segment.

Surgical Techniques: PLIF

A PLIF is performed from a posterior midline incision. In the PLIF, prior art cages are placed bilaterally, in a straight, anterior to posterior direction which is parallel to the sagittal plane, passing through the posterior muscles, past the spine's partially resected posterior elements, entering the spinal canal, past the dura containing its nerves and vessels, to enter the space between two vertebral bodies, called the interspace. To insert bilateral PLIF cages, the surgeon must therefore dissect the multifidus muscles from the lamina, the spinous process, with the undesirable consequences described above. The surgeon must then enter the spinal canal by resecting the ligamentum flavum, part or all of the lamina, part or all of the lateral facet joints, which are all themselves stabilizing elements, protecting the dural sac containing spinal nerves within the spinal canal. Then the dura must be retracted and the venous plexus that surrounds is cauterized to prevent excessive bleeding of structures directly connected to the central vascular system. The stabilizing posterior longitudinal ligament and part of the annulus fibrosis is partially or completely removed. Only after significant trauma to the muscles, after surgeon induced instability which in themselves may be of no therapeutic value, and after a significant loss of blood, can the surgeon begin removing the cartilaginous interbody disc to prepare the bed for the bilateral intervertebral PLIF cages. The cages are then inserted in straight posterior to anterior direction, parallel to the sagittal plane, from each side of the now exposed spinal chord. Most often, the PLIF cages are combined with pedicle fixation to compensate instability created by the partial or complete removal of the facet joints and the dissection of the longitudinal posterior ligament.

It is usually thought that the magnitude of the patient's problem justifies the amount of soft tissue destruction. In certain cases the surgeon desires to remove these structures in order to decompress a specific nerve for treatment. Still a bilateral PLIF procedure obliges the surgeon to perform dissections that in some situations may have no therapeutic value other than access for intervertebral cages. Posterior structures can be destroyed simply for posterior access to the anterior spine.

On the other hand, a PLIF spinal fusion construct in conjunction with pedicle fixation, results in a highly stable structure consisting of two bilateral supports between the vertebral bodies, with a bone inducing substance at an optimal location and pedicle fixation that serve as substitutes for destabilized facets. Surgeons have searched for the same therapeutic gesture, a similar biomechanical construct, but with less extensive trauma to the surrounding anatomy which need not to be touched for treatment. Because in some situations the midline approach PLIF dissects structures that would be good to leave intact, refined midline decompression and sagittal cage insertion methods have been created which are also used with pedicle fixation.

Surgical Technique: TLIF

Some patients present symptomatic pathology which is located predominantly on one side, requiring a destabilizing nerve decompression for treatment within the spinal canal, but only on one side. At the same time, the surgeon must build for fusion a stable biomechanical construct which is bilateral. The goal in such cases is to assure the treatment of the lesion, disrupt only the structures required for treatment on one side, but stabilize both. The unilateral Transforaminal Lumbar Interbody Fusion (called TLIF by some) was developed to treat such pathology. For this technique, the surgeon resects one entire facet joint on only one side and then inserts the cages through the space created. The procedure is called Transforaminal because the posterior aspect of the intervertebral foramen is formed by the facet joint. Once removed, the cage passes here. For the TLIF technique, cages therefore are inserted from one side, anterior or posterior, again in a direction parallel to the sagittal plane, but this time translated to the midline from the side of insertion.

It is important to note that although the TLIF inserts the cage from one side, where the facet has been resected, this procedure does not use the Extraforaminal Lumbar Interbody Fusion (ELIF) Surgical Plane, described below for the surgical approach of this invention. Thus, to gain access to the facet to be removed, the unilateral spinal canal and then the more anterior disc space, the multifidus must be dissected from the posterior elements, from at least one side, which is the same dissection for each side of a PLIF. One main difference between the TLIF as compared to the PLIF, is that only one side of the spinal canal is entered for decompression, disc access and then cage placement. This results in less blood loss and less potential trauma to the nerves.

A second main difference from the PLIF is that the TLIF usually resects one entire facet from the side which surgeon wishes to enter the canal. This gives access to the disc but is much more destabilizing than the PLIF which most often tries to conserve the lateral portion of each facet in an attempted compromise between neural decompression and biomechanical stability. The dura is then retracted to the midline and the venous plexus cauterized from one side. Next, the posterior longitudinal ligament is cut from its most lateral aspect to the midline. Again, this is a partially destabilizing maneuver, which should be justified only in terms of its therapeutic or biomechanical value and not simply for access to the spine. The posterior annulus is after cut from the ring apophysis at the midline and laterally to where the resected facet was located. The disc is then cleaned of its cartilaginous material and a first cage is placed via the transforaminal approach. With special instruments the first cage is laterally translated to the midline. A second cage is inserted, which, using the same instruments, pushes and translates the first, further to the lateral side.

In this manner, a bilateral cage construct is achieved from a midline posterior approach by using only one side entry through the spinal canal. Because a one stabilizing facet joint has been removed for cage entry and decompression, pedicle fixation must be added at this side to perform the breaking function of what has been removed. At times, unstable spinal conditions will oblige the unilateral TLIF surgeon, to insert his cages from one side of the spinal canal, but to place pedicle fixation in both sides. In these instances, the spinal canal is only approached and disrupted on one side, while the multifidus is disrupted bilaterally. Thus in the cases where bilateral pedicle fixation is performed with a TLIF, the goal for less trauma is achieved for only boney structures, ligament and neural structures, and not the posterior lumbar muscles.

Prior art methods using the posterior midline approach are usually most logically reserved for those cases where the pathology requires the surgeon to dissect the posterior elements, such as a portion of facet, to access the spinal canal where decompression must be achieved for the purposes of treatment and not only for stabilization with cages.

It should be noted that final placement in these prior art methods insert the cages in a straight line that is parallel to the sagittal plane. The medical term for "sagittal" is the plane anterior to the posterior. This describes the orientation of most bilateral cages inserted from a midline surgical approach, either using bilateral placement that is from both sides of the dura and the spinal canal for the PLIF, or unilateral lateral placement which results in a bilateral construct where cages are placed from one side of the spinal canal, and translated to the contra-lateral side as in the TLIF.

The extensive dissection of the posterior midline approach, with its destruction to the surrounding muscles, ligaments, vessels and nerves, has lead surgeons to explore other surgical techniques. As a means to place pedicle screws, percutaneous pedicle screw insertion methods have been developed using trocars. As the location of the pedicle cannot be directly visualized, a Kirshner wire is driven through the skin, using intra-operative x-ray fluoroscopy for each pedicle. Dilating trocars are placed over the Kirshner wire until a sufficient opening has been achieved for the pedicle screw to run through the trocar. A small but separate incision is made for each pedicle. Pedicle screws are inserted through the trocar into the pedicle of each vertebrae to be fixed, on each side of the patient. A special jig is attached, and through yet another stab incision a connecting rod is threaded through each screw connector, all of which is blocked into one joining construct.

While this technique has the merit of allowing the surgeon to build a pedicle fixation portion of his construct without dissecting the multifidus from the posterior elements, it is achieved at the price of six separate incisions for a construct of four pedicle screws. It indiscriminately splits muscles rather than separating muscle groups along the natural line cleavage created by the muscle fascia, protecting the muscles vascular and neural sources. With this technique, access to the spine and its pathology is indeed minimal, that is insufficient to access and treat many lesions. To reach the interspace for cage placement, separate incisions are required. To place bone graft at the facet joints, about the pedicle screw, separate incisions must be made. In addition, because the entry to the pedicles cannot be directly visualized, a great deal of radiation must be endured by both patient and surgeon, as each screw placement must most often be validated by x-ray fluoroscopy. New virtual technologies, which allow the surgeon to "see" screw placement on a video screen, are being explored as an alternative to radiation guidance for each percutaneous screw. But again these technologies require yet another incision to place special markers on the anatomical landmarks of the spine.

The above described limitations of the prior art caused the inventors to consider surgical approaches and technologies which instead of attempting to constrain the anatomy to an implant, used the body's natural delineations to achieve maximum access to the posterior spine, yet with minimal trauma. A stable fusion construct that reduces trauma allows the patient to move sooner, while protecting the fragile healing bone to improve the chances of the fusion growth and assure a life living bridge of bone. The surgical approach to make it possible should, wherever possible, limit dissection to the treatment of the pathology, without compromising the stability of the construct and the extent that the compressive pathology is removed. The resulting construct must respect the overall balance of the spine.

SUMMARY OF THE INVENTION

The present invention now provides a method for repair of a spine from a posterior approach, comprising the steps of:
a. making an incision in the skin lateral to the midline,
b. making an incision through the Erector Spinae Aponeurosis (ESA) following the ELIF groove,
c. separating the ESA from the Longissiumus Thoracis Pars Lumborum (LTPL),
d. atraumatic separating the Multifidus from the LTPL using interfascial boundary between the Multifidus and the LTPL, and
e. creating a surgical plane having an angle of 20° to 60°.

This invention provides a method with appropriate implants and instruments that allow the surgeon to access the posterior elements, the anterior spine and deep spinal pathology while leaving the surrounding structures functionally intact. At the same time the method according to the invention assures that the surgeon's treatment can be complete and uncompromised by his need to save surrounding tissue that does not concern the pathology. Thus, the disc, vertebral endplates, the pedicles, facets as well as the spinal canal are accessible.

For this invention, another bearing line has been created, the ELIF Lateral Trajectory Line originating from the anterior apophysis of the vertebral body, running posterior and lateral oblique at about 30° across the superior vertebral endplate, past a position, just lateral to the superior facet and therefore the mamillary process, which is a cordal insertion point for many multifidus muscles. This position is adjacent to an entry point to the pedicle, or a means of reaching the more medial spinal canal by passing through the facet joint. The ELIF Trajectory Line continues to extend dorsal laterally through the Erector Spinae muscles and tendons to the Iliac crest, emerging out through the skin.

For the purposes of this invention, it is called the ELIF Lateral Trajectory Line. It is the vector for passage, where the posterior approach surgeon may pass through intact muscles, past nerve roots to reach into the anterior spine without entering the spinal canal. As the posterior spinal structures cover each other and tend to overlap, the ELIF Lateral Trajectory Line cannot be followed in a straight path because this would injure the surrounding structures. Like the plumb line for the mason or the northern star for the sailor, the ELIF Lateral Trajectory Line serves the surgeon to orient himself and track progress as he navigates past and around the complex structures of the posterior spine using the methods described below.

The Interfascial Boundary

To reach the anterior spine from the posterior approach, it is possible to locate The Interfascial Boundary, and without trauma, to separate the Multifidus from the more lateral Longissimus Thoracis pars Lumborum LTPL, to reach the lateral aspect of the superior facet while leaving muscle fascicles intact upon their insertions. However, from the posterior approach, locating the Interfascial plane can be difficult, and approaching it from the wrong angle can make it impossible to complete the surgery which concerns this invention.

The Lumbar Back muscles and Fascia can be used to navigate from the posterior to the anterior spine in a safe and reproducible manner. The Multifidus, Lumbar components of the Erector Spinae, the Thoracic components of the Erector Spinae Aponeurosis ESA, as well as the Thoracolumbar fascia, are all separate structures, each with their own function. These can be preserved in posterior spinal surgery with the method and implants of this invention. Each structure is discernable due to their fiber orientation. They can be non-traumatically separated and used to navigate towards the Interfascial Boundary along the ELIF Lateral Trajectory Line in order to make the ELIF Surgical Plane.

ELIF Groove

The Erector Spinae Aponeurosis ESA must be passed through in a posterior approach in the spine. The ELIF groove appears as a valley in the Erector Spinae Aponeurosis and is used as a landmark for an incision and to locate the Interfascial Boundary.

The method to find the Interfascial Boundary and navigate through the lumbar back muscles and past the nerves to the anterior spine can be represented by a schematic resembling a staircase and taught as a series of clear steps, descending from the lateral aspect of the ELIF lateral trajectory at the iliac crest to the interdiscspace. This can be used to teach the ELIF Lateral surgery in a reproducible manner.

A further object of the invention is to provide an intervertebral implant for the method according to the invention. A preferred embodiment of the implant comprises a pair of dissimilar cages, wherein preferably both cages are curved.

DESCRIPTION OF THE PREFERRED EMBODIMENTS

Preferred embodiments of the invention are illustrated in the annexed drawings in which:

FIG. 1 illustrates surgical steps to enter the L4-L5 interdisc space;

FIG. 2 a transverse section through the L4-L5 interdisc space and muscles on the posterior side of the spine, showing where the first incision is made through the skin, fat and the thorical lumbar fascia;

FIG. 3 a section according to FIG. 2, illustrating the steps of retracting the skin, fat and thorical lumbar fascia medial to the ELIF groove to find the interfascial boundry;

FIG. 4 a section according to FIG. 2 showing the steps of separating the ESA from the Longissimus Thoracis Pars Lumborum (LTPL) and separating the Multifidus from the LTPL using the interfascial boundary between the Multifidus and the LTPL;

FIG. 5 a section according to FIG. 2, illustrating a bilateral approach of the spine;

FIG. 6 a section according to FIG. 2, wherein a pedicle screw is placed;

FIG. 7 a section according to FIG. 6, showing a cut through the intertransverse ligament and the direction of the access to the disc;

FIG. 8 a section according to FIG. 2, wherein a pair of intervertical implants are inserted between adjacent vertebrae;

FIG. 9 illustrates the superficial muscles of the back and a thorical lumbar fascia FIG. 10 a posterior view of the spine;

FIG. 11 a posterior view of the spine and the left part of the Erector Spinae muscles, which compose the Erector Spinae Aponeurosis (ESA);

FIG. 12 a close-up view of FIG. 11 showing the incisions of the invention;

FIG. 13a-13b a transverse section through the spine showing the steps of inserting cages into the intervertebral space between adjacent vertebrae with a unilateral approach;

FIG. 14a-14b a transverse section through the spine showing alternative steps using a unilateral approach to insert a pair of implants into the intervertebral space between adjacent vertebrae, with entry into the spinal canal to the spinal canal stenosis;

FIG. 15 a transverse section through the spine illustrating a bilateral approach, without entry into the spinal canal;

Figure 1:
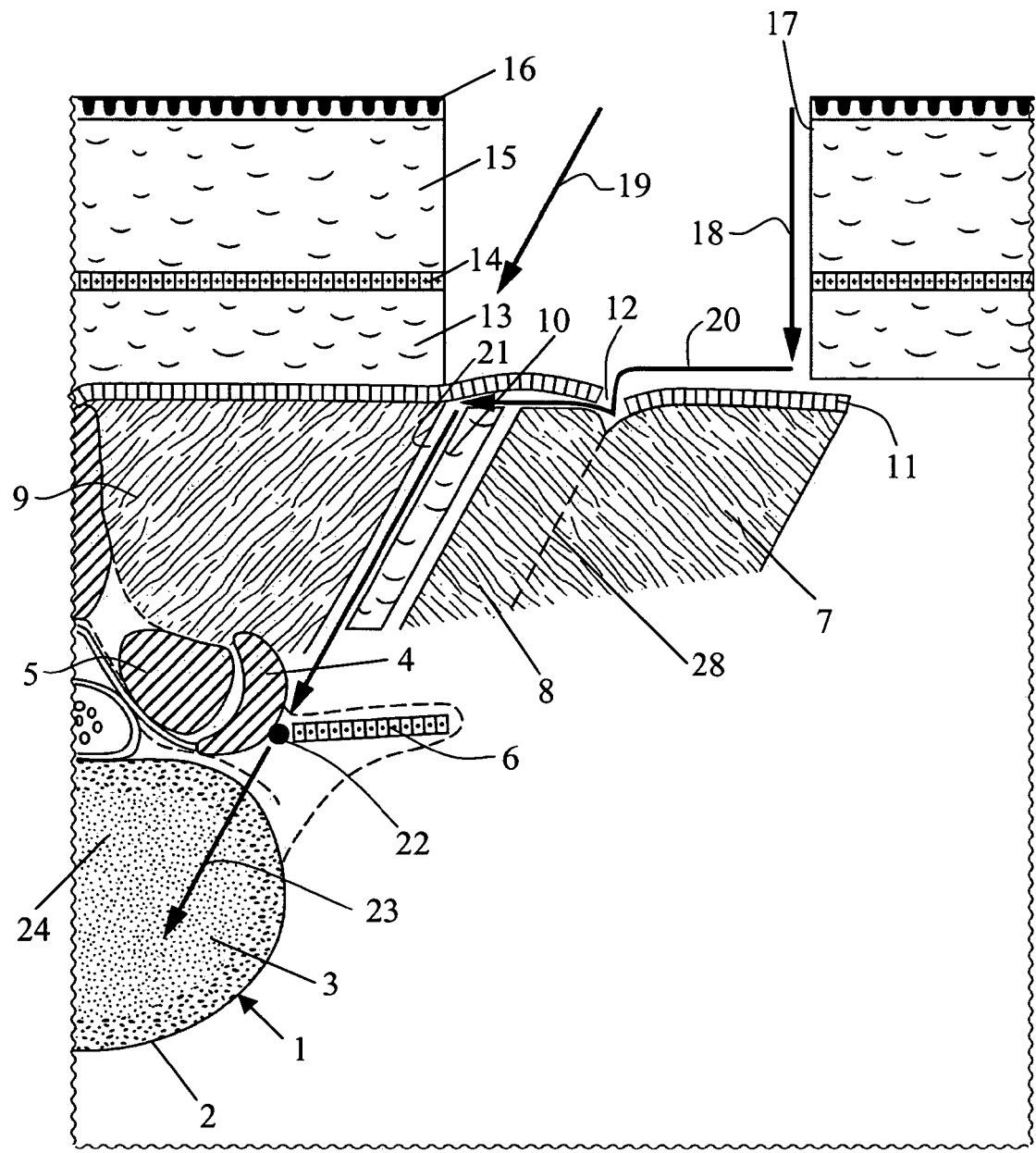
Figure 2:
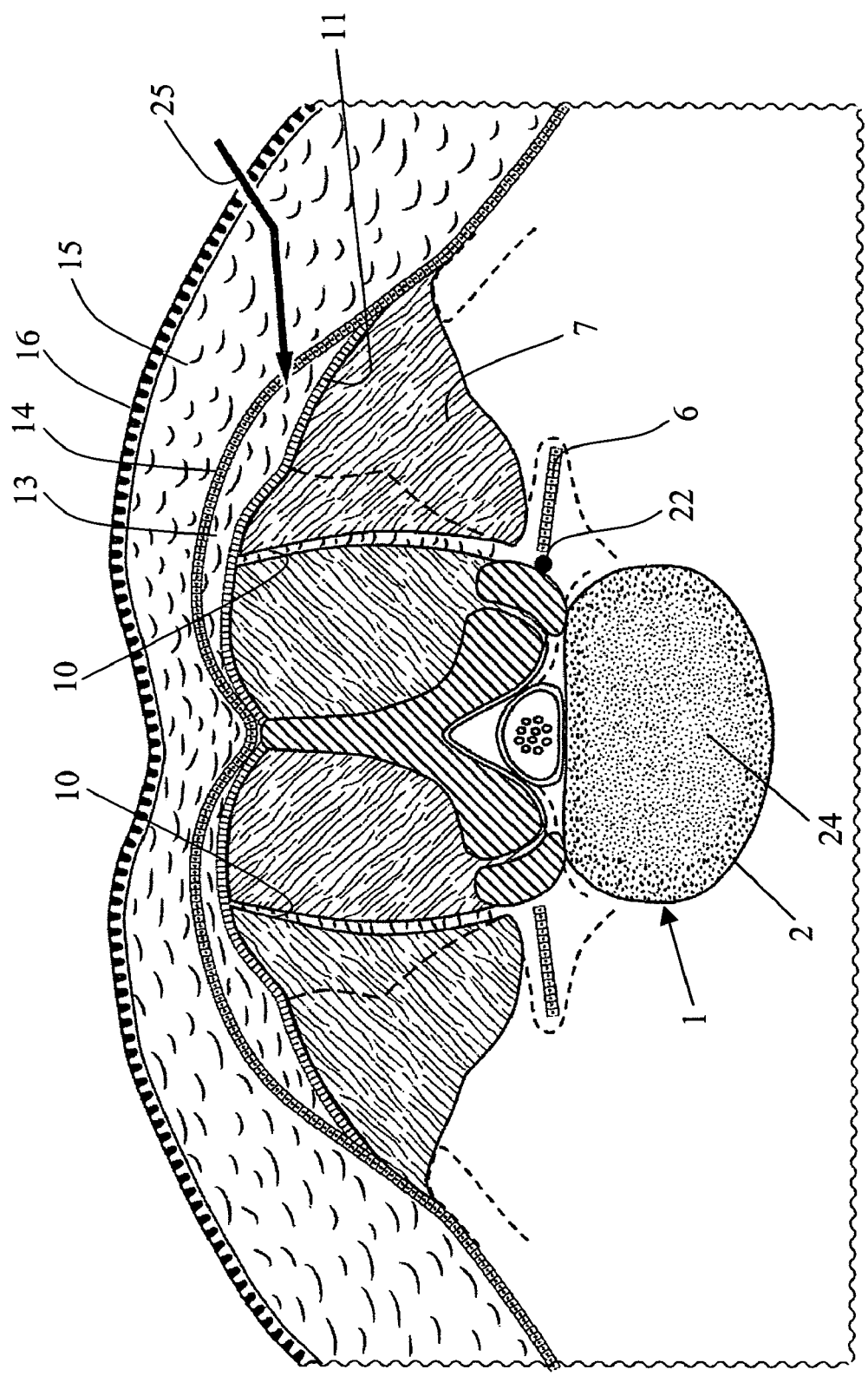
Figure 3:
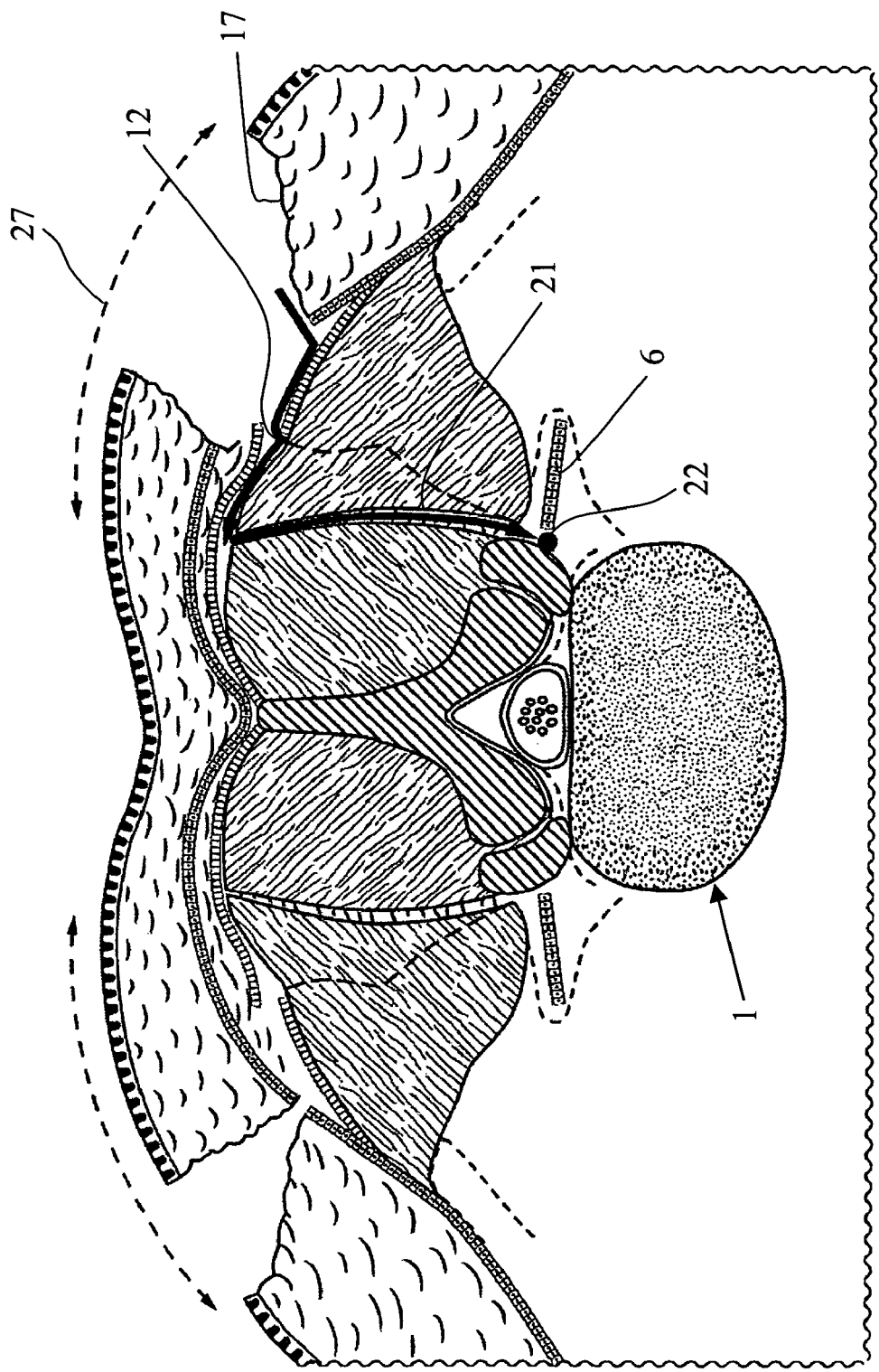
Figure 4:
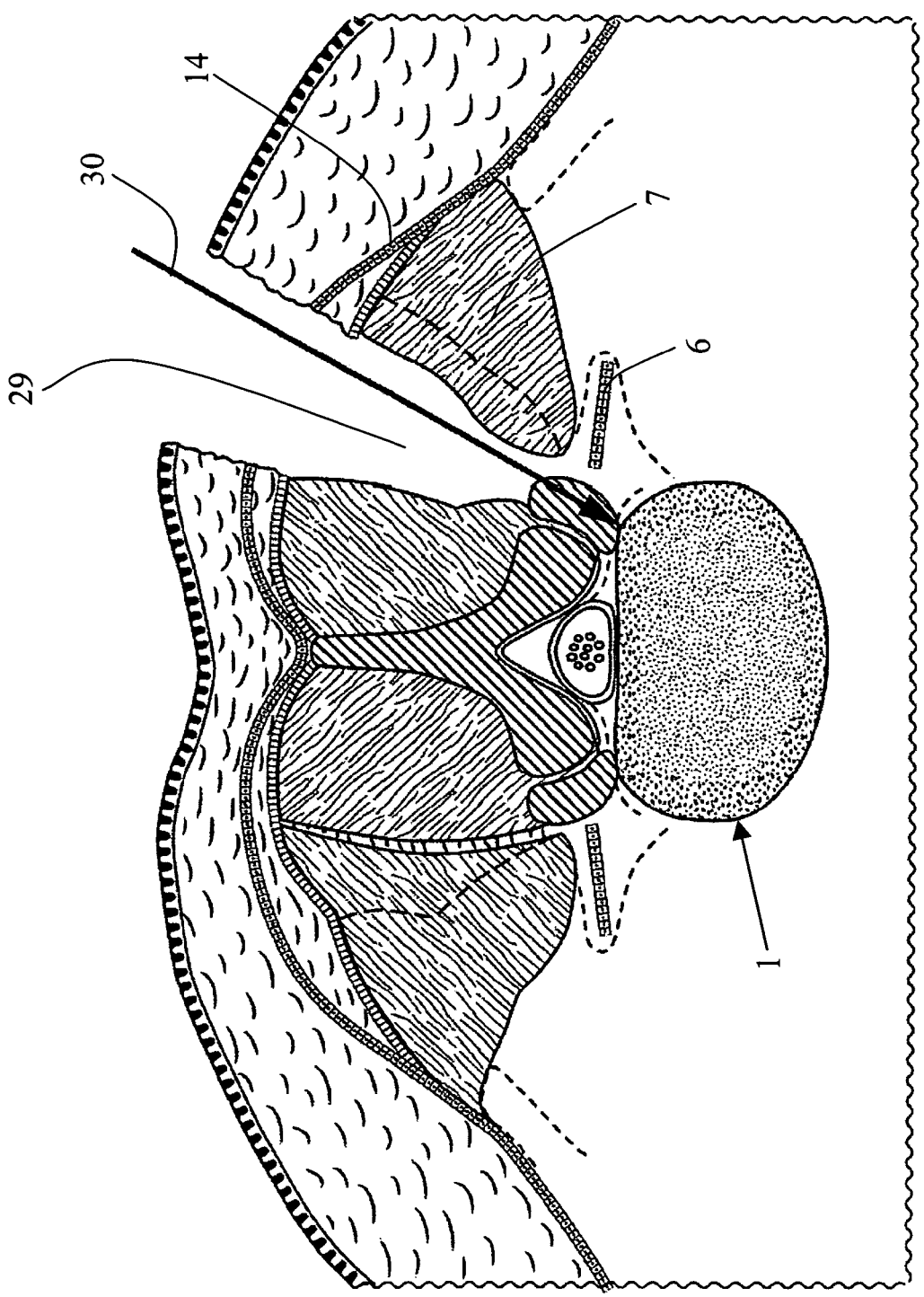
Figure 5:
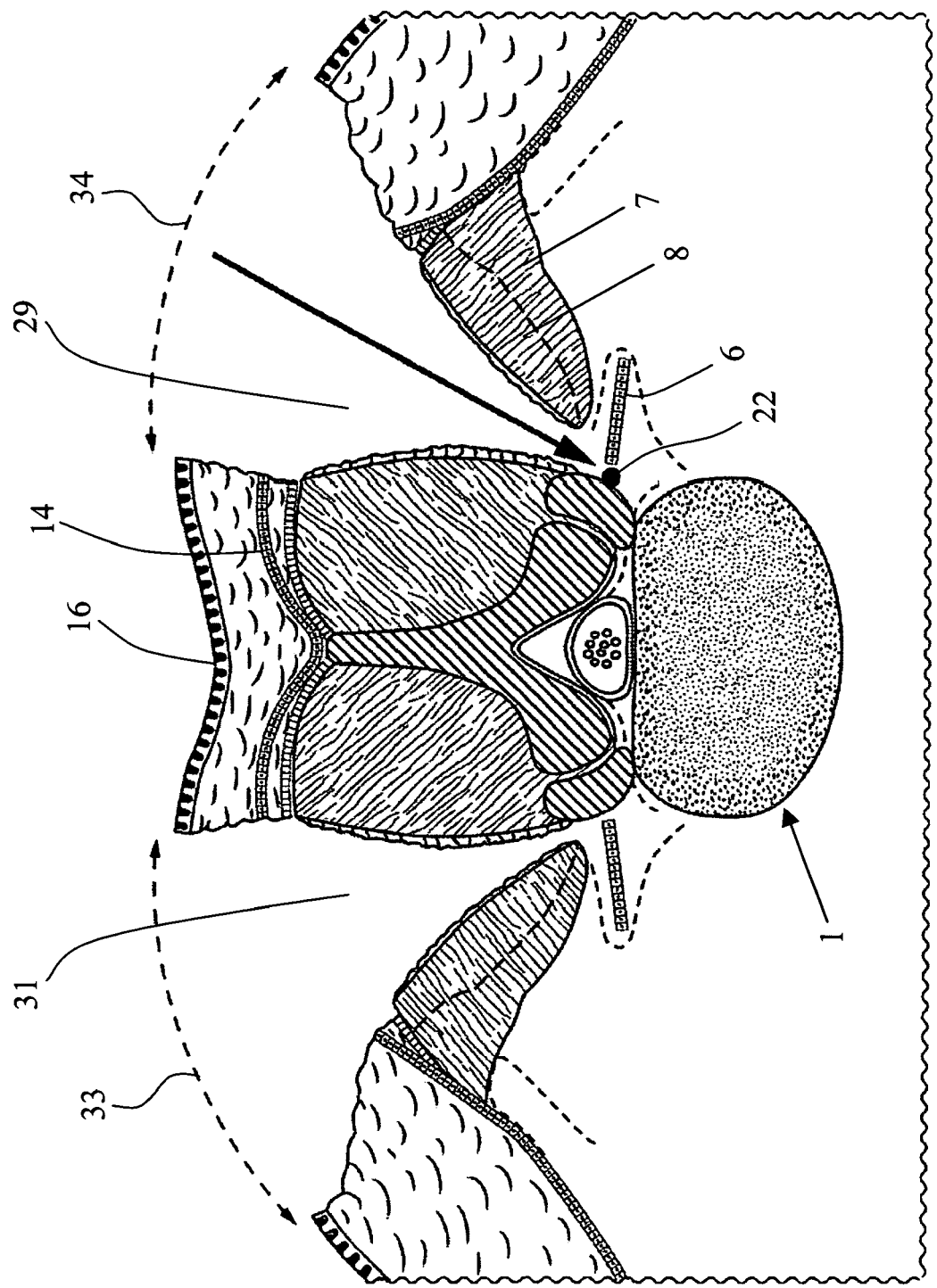
Figure 6:
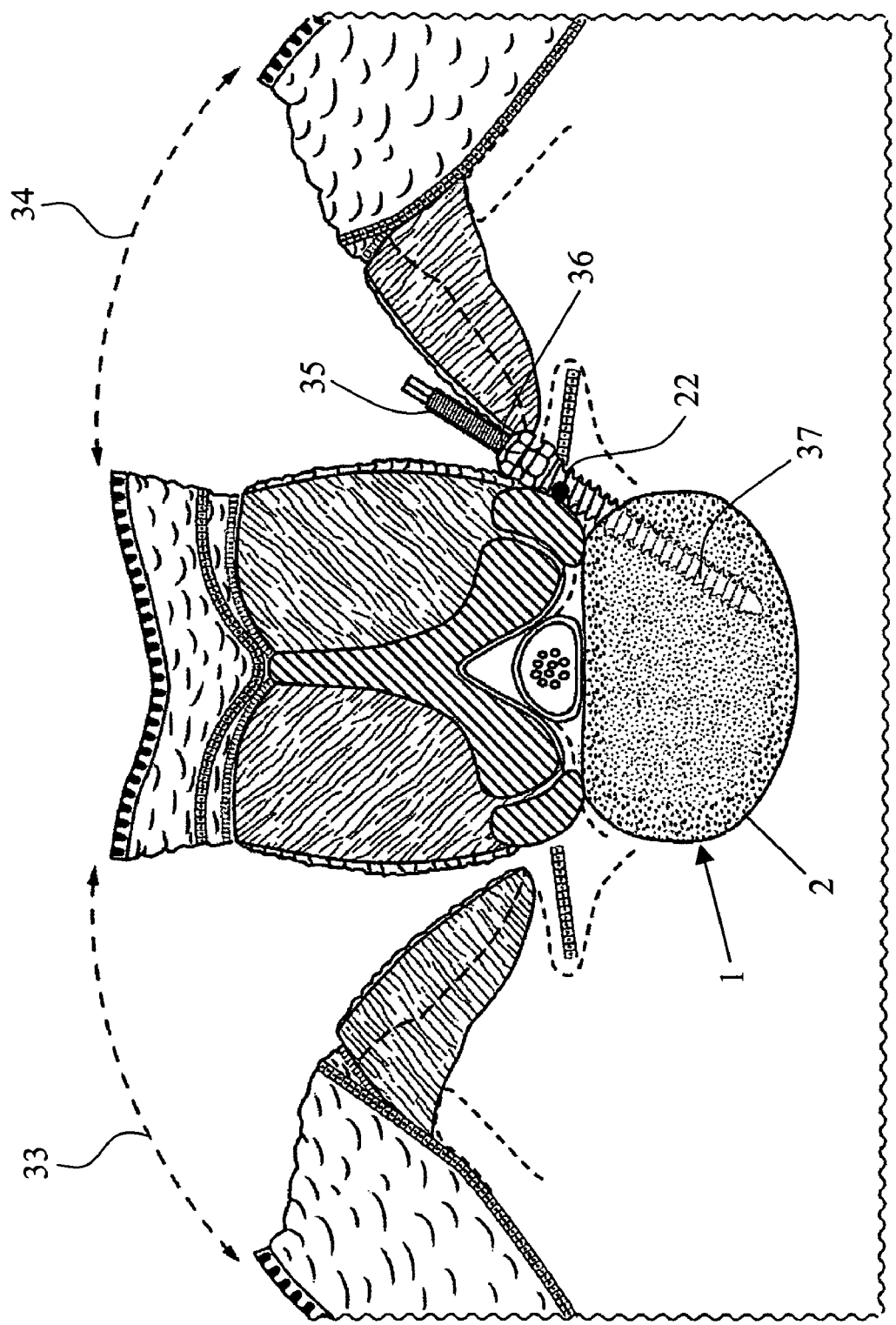
Figure 7:
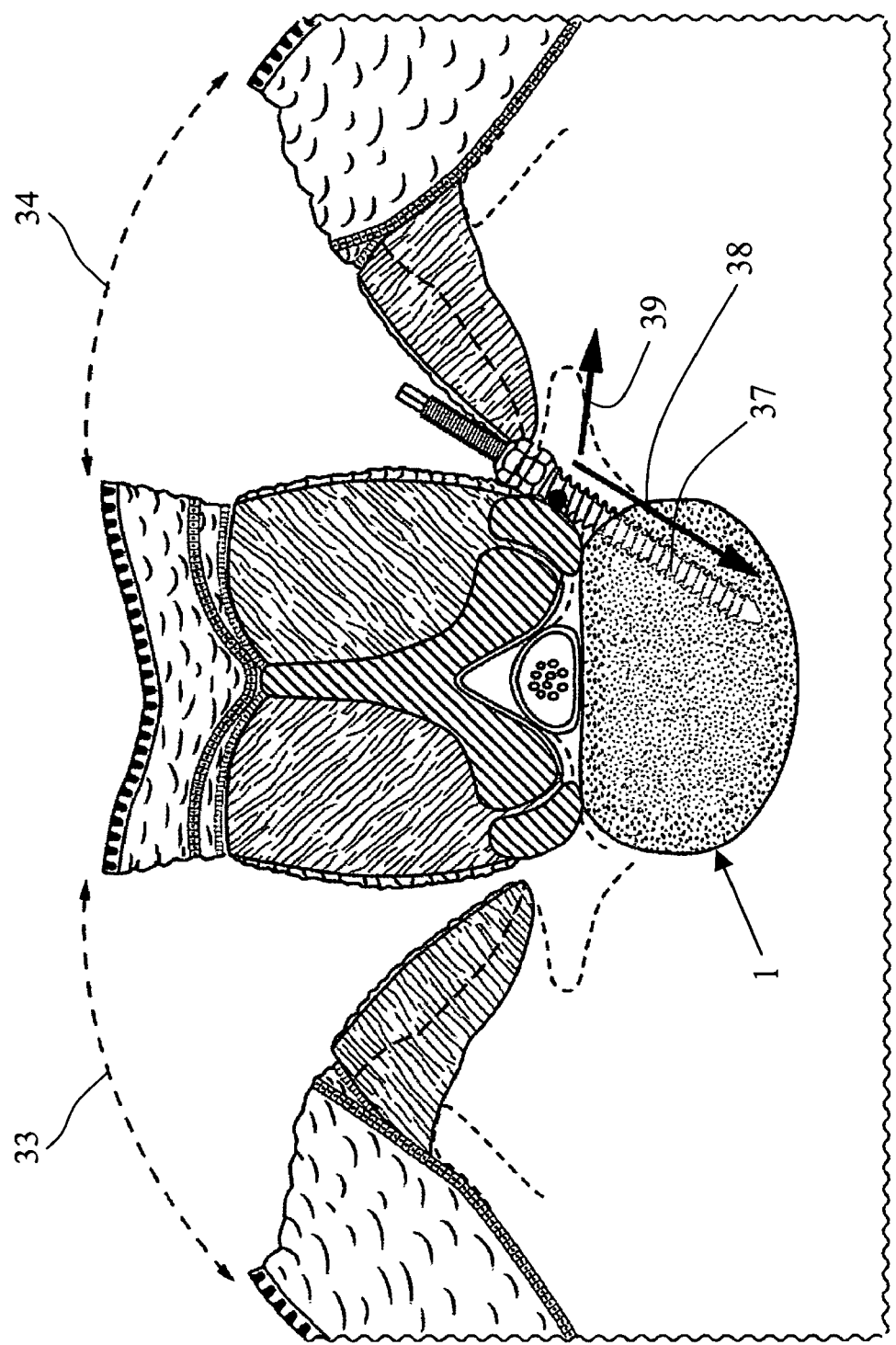
Figure 8:
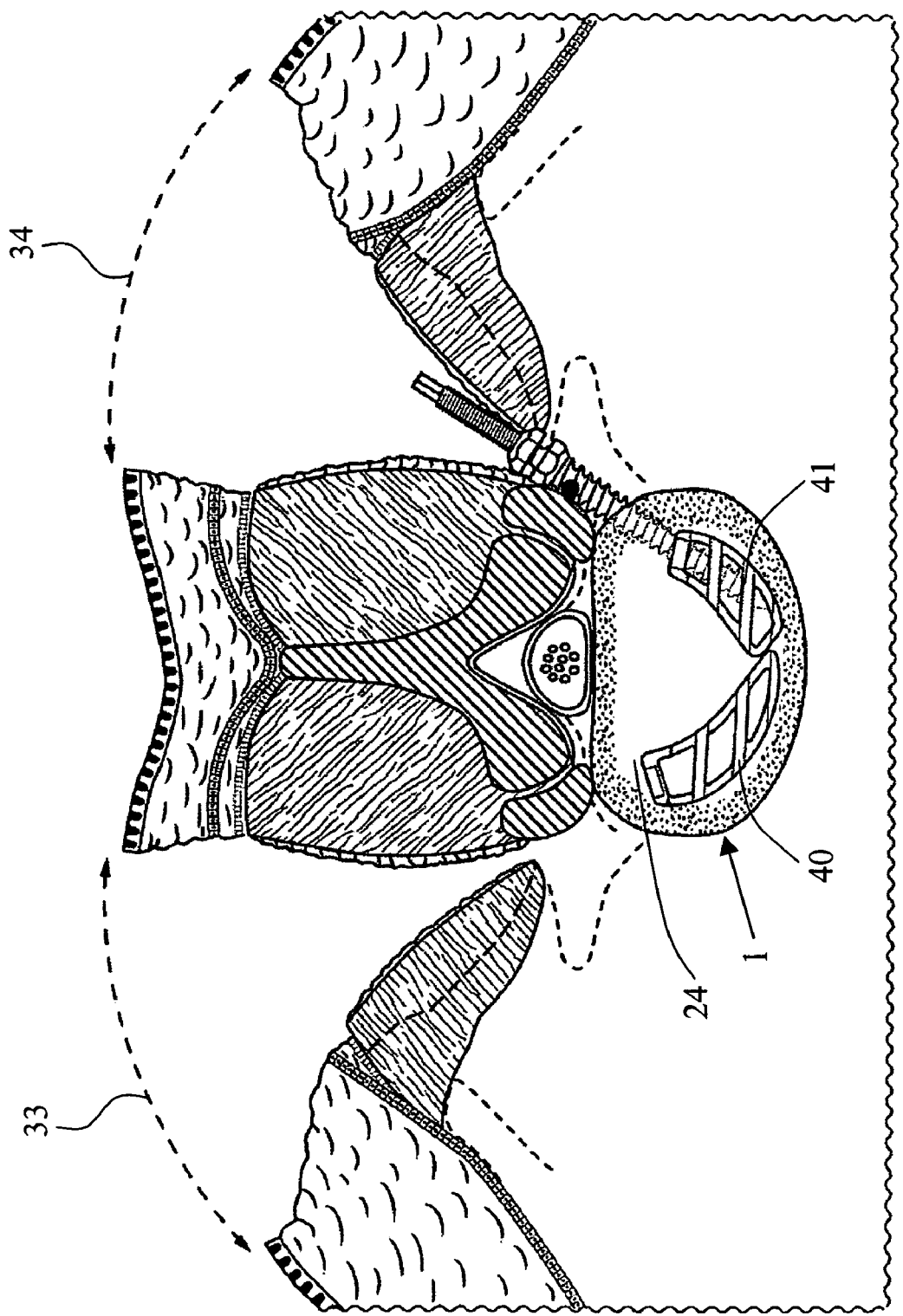
Figure 9:
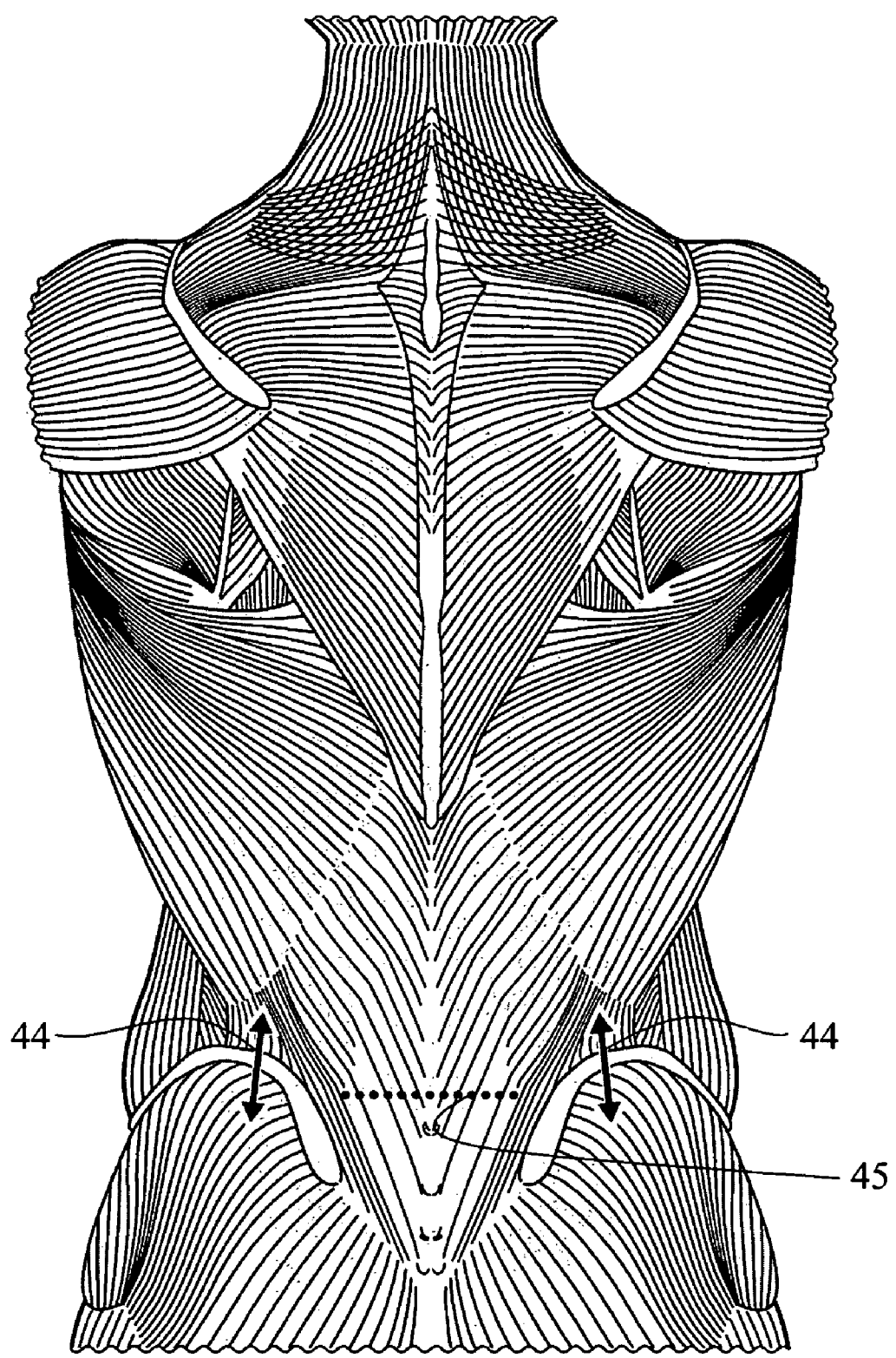
Figure 10:
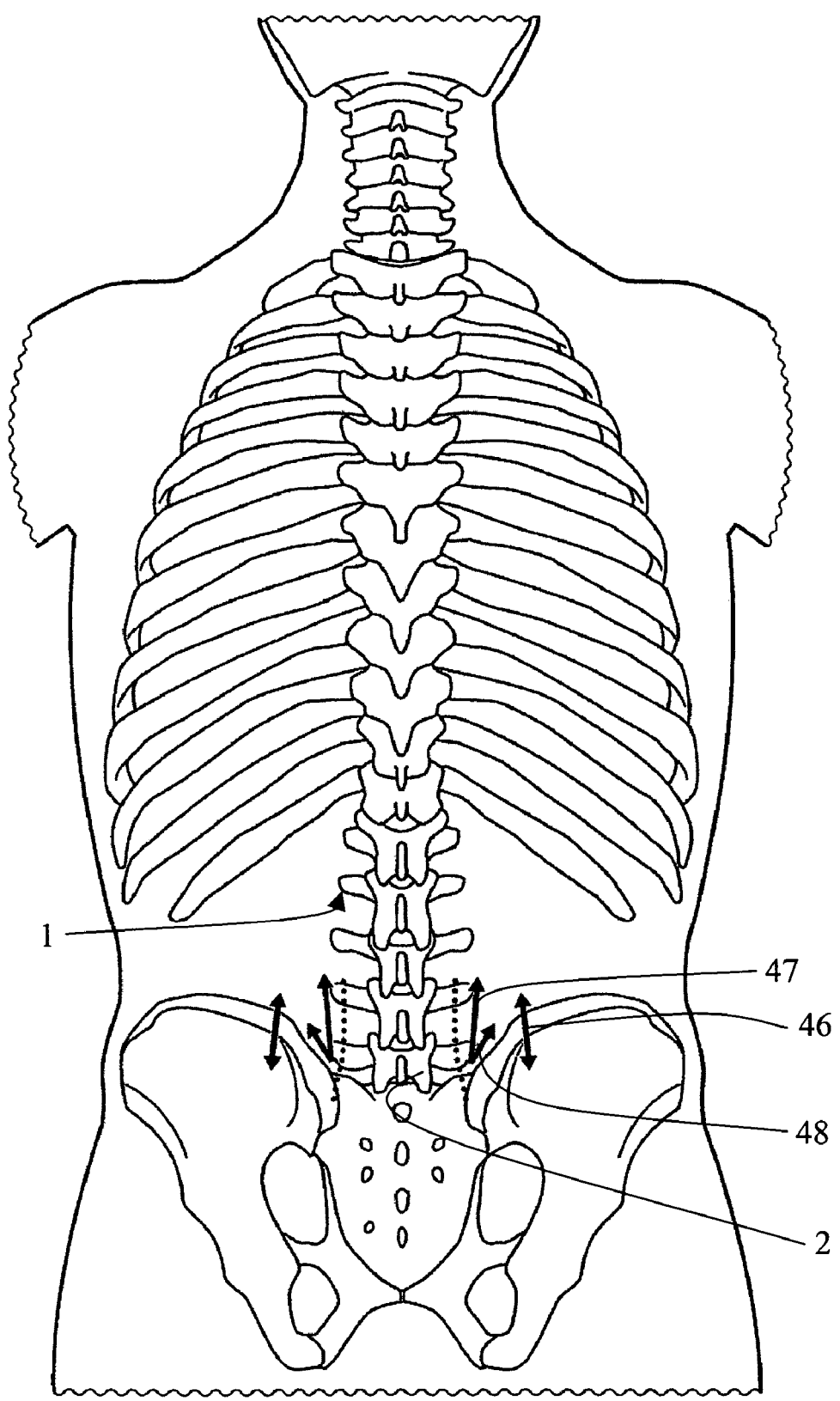
Figure 11:
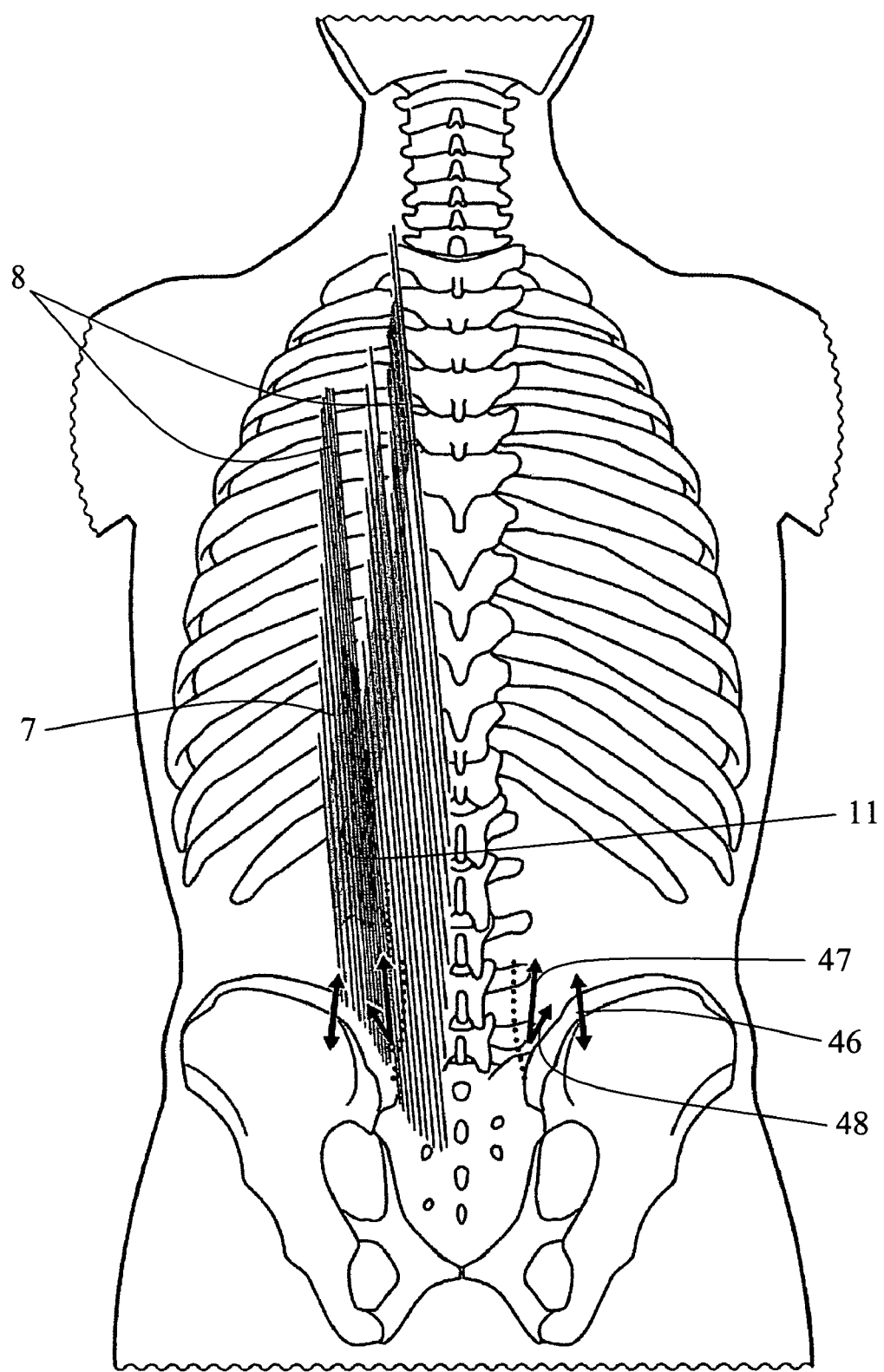
Figure 12:
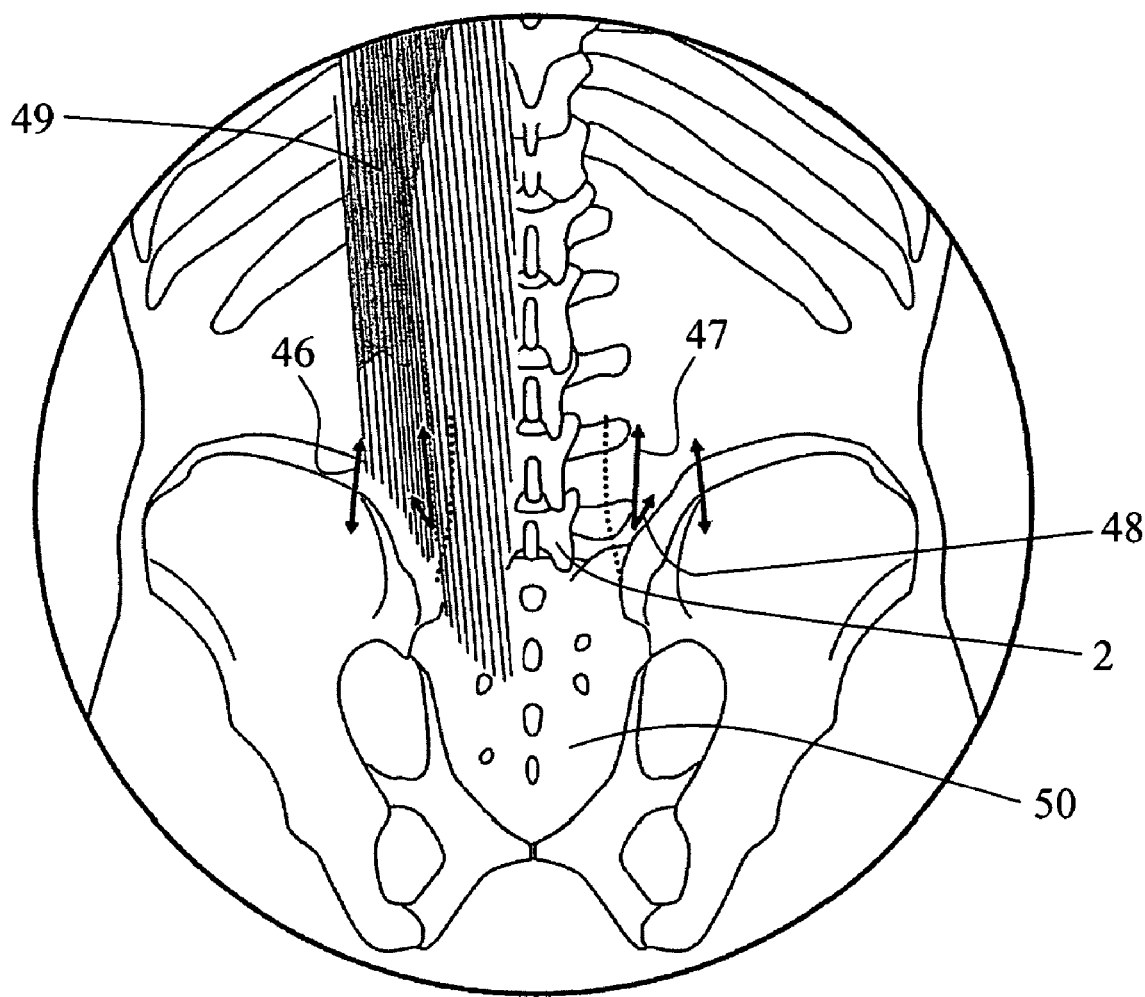

FIG. 1 as well as the following FIGS. 2 to 8 illustrate the steps for locating screws 35 and a pair of cages 40 and 41. The cages 40 and 41 are inserted into an interdisc space 24 between adjacent vertebrae 2 of spine 1. The steps include an incision 17 into the skin 16 in direction of arrow 18, an incision through the Erector Spinae Aponeurosis (ESA) 11, following the ELIF-Groove 12, separating the ESA 11 from the Longissimus Thoracis Pars Lumborum (LTPL) 8, separating the Multifidus 9 from the LTPL 8 using the Interfascial Boundary 10 between the Multifidus 9 and the LT 8 and creating a surgical plane as indicated with line 30 in FIG. 4. This surgical plane has an angle of 20° to 60°, preferably approximately 30° to the sagittal plane. One important aspect of the invention is the muscle split between the Multifidus 9 and the LTPL 8 and the way to get there safely in order to preserve the fascia.

Like all muscles, the Multifidus 9 and the adjacent Longissimus Thoracis Pars Lumborum 8 are each surrounded by separate deep muscle fascia. In addition, between the Multifidus 9 and the Longissimus Thoracis Pars Lumborum 8 fascia can be found a fatty Interfascial Boundary 10. This structure can be used to create what is called the ELIF Surgical Plane. The Interfascial Boundary 10 can be observed in most preoperative Magnetic Resonance Imagery (MRI) but has been found difficult to locate in surgery. Using the methods described below that are part of the invention, the surgeon may find the Interfascial Boundary 10 and separate the Multifidus 9 and the Longissimus Thoracis Pars Lumborum 8 using only a compress, without damage to fascia, muscle, vessel or nerve and thus create the ELIF Surgical Plane. For ELIF cage surgery and this invention, this is a non-traumatic passage way to the joint capsules, facets, pedicles, spinal canal as well as the anterior spine and can be used to treat pathology while disturbing the surrounding structures in a minimal way.

The Erector Spinae Aponeurosis (ESA) 11 is a flat tendinous sheet that covers the Lumbar Multifidus 9 and the lumbar components of the erector spinae muscles, that is the Longissimus Thoracis Pars Lumborum 8 and the Iliocostalis Lumborum Pars Lumborum. From the midline tips of the Lumbar Spinous Processes, it laterally spans over the back muscles to insert into a dense fascial seam which is called the Lateral Raphe. The fibers composing this wide tendon sheet run longitudinally, downward and convergent in relation to the midline, depicting the forces they resist between the thoracic and lumbar spine where they insert into the Spinous Processes of the Lumbar Vertebra and Sacrum, the Posterior Iliac Spine and Crest. Careful dissection of its origins at the Thoracic Spinae will reveal that the most medial tendons emerge from the high thoracic vertebra at the level of the shoulders. The more lateral tendons find origins at the ribs. The small muscles bellies of the formed in between are again quite separate from the Lumbar Erector Spinae muscles and the Multifidus muscles 9 this tendon sheet covers.

This Erector Spinae Aponeurosis (ESA) 11 is formed by an aggregate assembly of tendons formed by the Thoracic (not lumbar) components of the Erector Spinae muscles. The Thoracic components connect the lower back, the Ilium, the Sacrum and the Lumbar Spinous processes to the thoracic spine and are free to slide over the lumbar components of the Erector Spinae and Multifidus muscles. From a schematic perspective, one can imagine the thoracic components of the Erector Spinae muscles to function like a series of pulleys over its lumbar components, where the lumbar component muscles perform direct action upon the lumbar vertebra, and where the thoracic muscle components of the Erector Spinae act more directly upon the thoracic spine. For the surgical method, which is part of the invention, the Erector Spinae Aponeurosis (ESA) 11 is used as a landmark to find other structures it covers, the Erector Spinae Muscles Lumbar Components. It is also a structure that the methods, instruments and implants of the invention are designed to better save. A surgeon must understand the form and function of the Thoracic Erector Spinae Muscles and the Erector Spinae Aponeurosis (ESA) 11 in relation to the other lumbar spine muscles to use the methods, novel implants and instruments that are part of the invention.

Two muscles make the thoracic components of the Erector Spinae: the medial Longissimus pars Thoracis 8 and the adjacent, more lateral Iliocostalis Lumborum pars Thoracis. Their caudal or lower aspects assemble side to side in a common flat assembly of tendons to form the Erector Spinae Aponeurosis (ESA) 11.

The highest or most rostral fascicles of the Longissimus pars Thoracis 8 first begin as a ribbon like tendons, which are about 3 to 4 mm long and at T1 or T2 emerge from the Transverse Processes of the Thoracic Vertebra. The then form muscles bellies of 7 to 8 mm in length, which in turn extend as a long and flat caudal tendons, the first and most medial terminating into the L5 Spinous Process. Subsequent Thoracic fascicles of the Longissimus pars Thoracis exit from the next lower Thoracic Vertebrae in the same manner with their caudal tendons inserting in the spinous processes of a vertebra at levels further and further down. The cordal tendons from the highest thoracic vertebra can measure 24 cm in length, and as their origins begin further down the Thoracic Spine, the become shorter.

At about T5, the rostral tendons of the Longissimus Thoracis pars Thoracis have two insertions for origin, one at the transverse process of the Thoracic Vertebra and another more lateral insertion at the rib, making their muscle bellies y shaped. Thus, fascicles of the Longissimus Thoracis pars Thoracis extend from each subsequent Thoracic vertebra and with their caudal tendons merging in sequence to the adjacent medial tendon having its origins at the previous level, and inserting into spinous processes lower and lower upon the spine. In this manner, each of the 11 or 12 caudal tendons from the Longissimus Thoracis pars Thoracis 8 form the medial portion of an aggregate sheet, named Erector Spinae Aponeurosis (ESA) 11. Its medial tendon originates from T1 or T2, and most lateral tendon having its origins at the transverse process and rib of T12.

The cordal terminations of the Longissimus Thoracis pars Thoracis 8 attach to the Lumbar Spine, Sacrum and Illium in a serial sequence beginning at the Spinous Processes high on the Lumbar Spine 2, continuing to the Sacrum and the vicinity of the Posterior Superior Iliac Spine. For example, the fascicle which emerges from the highest thoracic vertebra (T1 or T2) also creates the most medial caudal tendon which composes the Erector Spinae Aponeurosis (ESA) 11 and terminates most often about at the level of the L1 spinous processes. Fascicles originating from each subsequent thoracic vertebra lower down the Thoracic Spine create the next lateral caudal tendon, which forms the Erector Spinae Aponeurosis (ESA) 11 and terminates in turn at the spinous process a lower lumbar vertebra. Thus, in the previous example, the fascicle originating from the next T3 vertebra would form a caudal tendon that runs adjacent to the one originating at T2, and then terminate at the next available spinous process bellow or at about the L2 level; the fascicle originating from T4 vertebra would terminate about at the L3 level spinous process, and so on. This sequence continuing in this manner until the caudal tendons from about T7 and T9 attach to the S4 spinous process. The T10-T12 fascicles insert on the dorsal surface of the sacrum extending laterally to the Posterior Superior Iliac Spine. The T12 caudal tendon is the most lateral component of the Longissimus Thoracis pars Thoracis 8 and most importantly to this invention, also merges with the Lumbar Intermuscular Aponeurosis (LIA) described above, thus attaching the Erector Spinae Aponeurosis (ESA) 11 and forming a groove, which for the purposes of this invention, is called the ELIF Groove 12.

Aside from its connection to the Lumbar Intermuscular Aponeurosis (LIA), the Erector Spinae Aponeurosis (ESA) 11 is thought to have no other significant attachments to the more ventral Longissimus Thoracis pars Lumborum 8, the Multifidus 9 or the Iliocostalis Lumborum pars Lumborum. These facts are employed in the methods of this invention. It is a goal of this invention to preserve the separate structure, movement and function of both the Thoracic and Lumbar components of the Erector Spinae muscles and tendons.

Separated from the Longissimus Thoracis pars Lumborum 8 by the Lumbar Intermuscular Aponeurosis, the second Thoracic Erector Spinae muscle is formed by the more lateral Iliocostalis Lumborum pars Thoracis 7. It is also composed of a rostral and caudal tendon, a muscle belly there between. Beginning most often at T4 or T5, the most rostral tendons of the Iliocostalis Lumborum pars Thoracis 7 emerge from the rib and extend some 9 to 10 cm in length, forming their muscle bellies of about 8 to 10 mm to continue as caudal tendons which compose the more lateral band of the Erector Spinae Aponeurosis (ESA) 11. Its first and most rostral (T4 or T5) fascicle is also the most medial component of the Iliocostalis Lumborum pars Thoracis 7, merging at the Erector Spinae Aponeurosis (ESA) 11 with the caudal tendon from the Z12 Longissimus Thoracis pars Thoracis, and therefore in the lower region, the Lumbar Intermuscular Aponeurosis (LIA). The most caudal aspect of these three structures all insert in close vicinity at the base Posterior Superior Iliac Spine, forming there a common point of anchorage. During muscle contraction, the Lumbar Intermuscular Aponeurosis serves to keep all of the Lumbar back muscles anchored close to convex form the lumbar spine with its lordotic curvature.

Longissimus Thoracis pars Thoracis fascicles 8 continue to emerge from each subsequently lower rib (T6 to T12) at more and more lateral attachments, forming their muscle bellies and the next lateral cordal tendons of the Erector Spinae Aponeurosis (ESA) 11. These terminate in sequence beginning at the base of the Posterior Superior Iliac Spine, and continue up along the dorsal edge of Iliac Crest.

The Erector Spinae Aponeurosis as a Surgical Landmark

The most caudal components of the Thoracic and Lumbar Erector Spinae muscles converge to a common region at the base of the Posterior Superior Iliac Spine, just lateral to the fascicles of the Multifidus 9, which cover most of the dorsal Sacrum. The Multifidus muscle 9 therefore is widest at its caudal base, becoming gradually more narrow approaching the L1 level. When seen from the posterior view, this gives an outline of the Interfascial Boundary 10 between the Multifidus 9 and the Longissimus Thoracis pars Lumborum 8 a sloping aspect, with the widest portion beginning at the Posterior Superior Iliac Spine, and most rostral sloping to the midline towards L1. This inferior lateral to superior medial line must be mentally in order to use the methods and implants of this invention, for it is through the Interfascial Boundary 10 that the surgeon must form the ELIF plane to non-traumatically approach the spine.

The Erector Spinae Aponeurosis (ESA) 11 covers the Longissimus Thoracis pars Lumborum 8. Seen from the surgeon's perspective, a distinct valley appears in the Erector Spinae Aponeurosis (ESA) 11, caused at the location of the Lumbar Intermuscular Aponeurosis and apparent through converging blood vessels. For the purpose of this invention, this is called the ELIF Groove 12, which from the Posterior Superior Iliac Spine, extends in medial to lateral orientation towards the thoracic spine. This groove 12 and its medial and lateral orientation is caused by rostral origins of the Thoracic components of Longissimus Thoracis 8 and Iliocostalis 7 which converge from separate vectors to a common caudal anchorage at the Posterior Superior Iliac Spine. The ELIF Groove 12 is an anatomical landmark used for the methods, instruments and implants of this invention.

A fascial structure called the Thoracolumbar Fascia envelopes the muscles of the posterior lumbar spine and is composed of the anterior, middle and posterior layers. Fascia from the Quadratus Lumborum derive the Anterior Layer of the Thoracolumbar Fascia, covering the anterior surface of this muscle, and attaching medially to the anterior surfaces of the transverse processes. At the space between the intertransverse processes, it can be considered as a lateral extension of the intertransverse ligament. The Middle Layer lies dorsal to the Quadratus Lumborum with its medial aspect attached to the tips of the transverse process, and directly continuous to the Intertransverse Ligament. This blending with several structures, making its origin and purpose a subject of anatomist debate, but which is none the less encountered in this invention. The Thoracolumbar Fascia's Posterior Layer extends from the tips of the spinous processes, covering the back muscles to blend with its medial and anterior layers near the lateral border of the Iliocostalis Lumborum, into what is often called the Lateral Raphe. The posterior layer of the Thoracolumbar Fascia is made of two layers, superficial and deep, with its fibers oriented in different directions, expressing the forces exerted upon them. The deep lamina of the Thoracolumbar Fascia have fibers which run caudallaterally (descending from the midline as they extend laterally) as in a thin wire like bands from each spinous process to insert into the posterior Iliac spine for those originating from the lower lumbar vertebra and into the lateral Raphe for those originating at more rostral attachements upon the spinous process of the lumbar spine. The superficial lamina run from their spinous processes from S3 to upper lumbar vertebra, in a caudalmedial (rising from the midline as they extend laterally) direction, connecting to the Latissimus Dorsi, Lateral Raphe. Together the various layers of the Thoracolumbar Fascia forms a retinaculum or a band like structure which holds the lumbar back muscles against the spine, and serving as anchorage for surrounding muscles acting upon distant structures. Furthermore, its fibrous bands are similar to ligaments and have a stabilizing role on the lumbar spine. Preserving the stabilizing role of the Thoracolumbar Fascia is an objective of this invention.

Role of the Lumbar Back Muscles, Erector Spinae Aponeurosis and the Thoracolumbar Fascia The posterior spinal muscles (Multifidus 9, Longissimus Thoracis Pars Lumborum 8, Iliocostalis Lumborum pars Lumborum 7) primarily exert an earthward and posterior force upon the posterior elements. This earthward force is mediated through the pedicles to the vertebral body 2 and the intervertebral discs, creating natural lordosis, postural balance, and as the patient bends forward, a braking motion. Some liken the action of the Multifidus 9 to the tensile action of a bowstring on a bow. Because each component fascicle of the multifidus muscle 9 radiates from the posterior elements of one vertebra 2 to several others below, each component fascicle influences several vertebrae and balance of the entire spine. These downward forces create lordosis that allows humans to stand upright an carry their heads above the shoulders. Therefore, the damage of one fascicle or fascia (for example by dissection of a surgical approach) can affect the balance and functions of many motion segments. The ability to better preserve the posterior back muscle structures, their vascular and neural sources, and therefore muscular function is addressed, with this invention.

With the steps described above a lateral trajectory line is created originating from the anterior ring apophysis of the vertebral body at the midline, running posterior and lateral oblique at about 30° across the superior vertebral endplate 3 to a position 22, just lateral to the superior facet. This position 22 is adjacent to an entry point of a superior articular process 4. The lateral trajectory line is shown in FIG. 1 with arrows 18, 20, 21 and 23.

After the interdisc space 24 is reached, pedicle screws 35 are placed for distraction of the motion segment and later fixation if required. Now cages 40 and 41 are placed unilaterally as shown in FIGS. 13a to 13c and 14a and 14b or bilaterally as shown in FIG. 15. The screws 35 will serve first to hold the interdisc space 24 open during the placement of the cages 40 and 41, and later for pedicle fixation in cases where the additional stability or manipulation of a segment is desired.

Figure 13A:
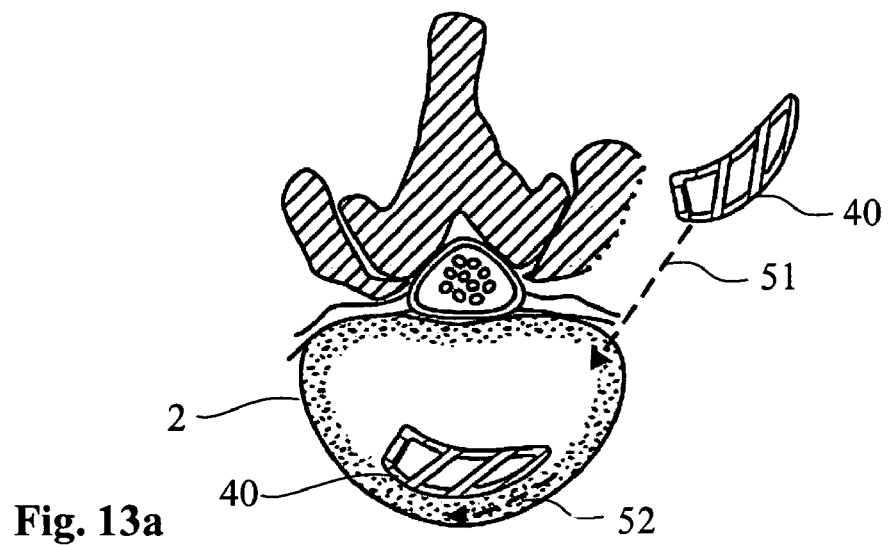
Figure 13B:
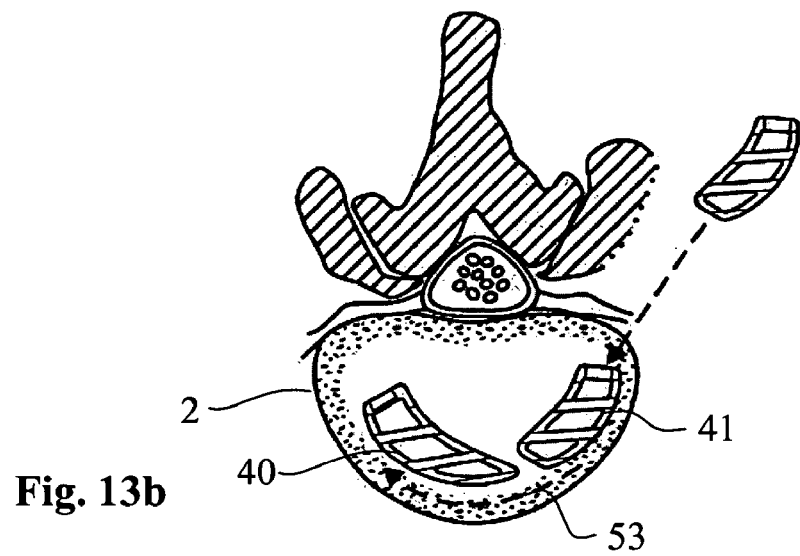
Figure 13C:
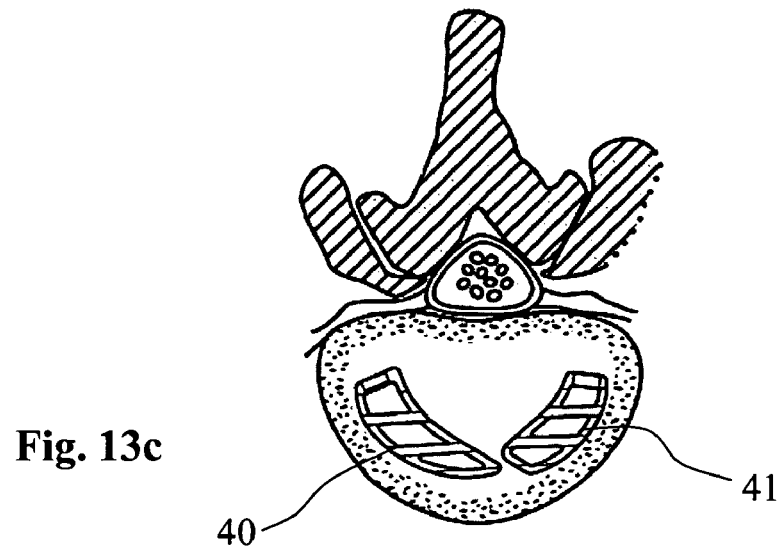

With the unilateral approach as shown in FIGS. 13a to 13c and FIGS. 14a and 14b a biomechanical construct can be achieved with one incision. The first cage 40 is inserted and moved within the interdisc space 24 according to arrows 51 and 53 as shown in FIGS. 13a and 13b. The second cage 41 is now inserted to a point where its leading edge mates with the first cage 40.

Figure 14A:
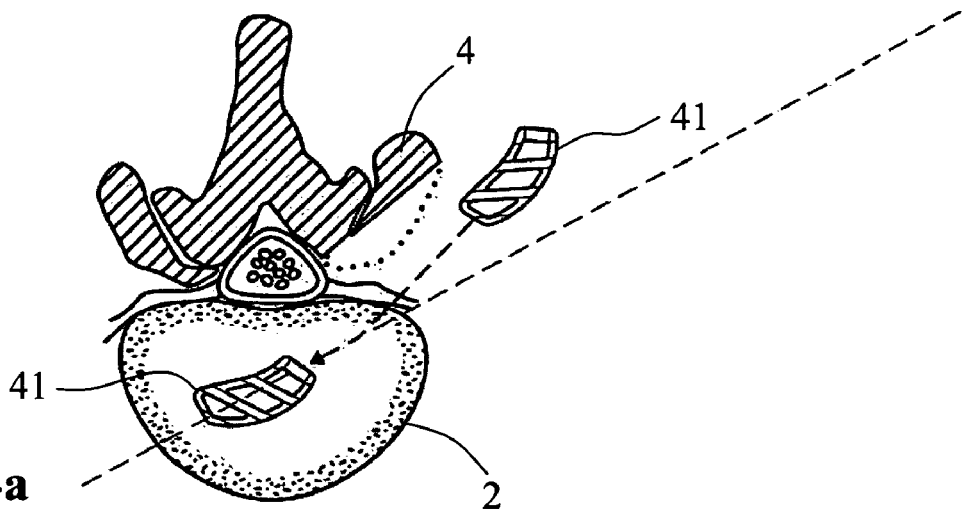
Figure 14B:
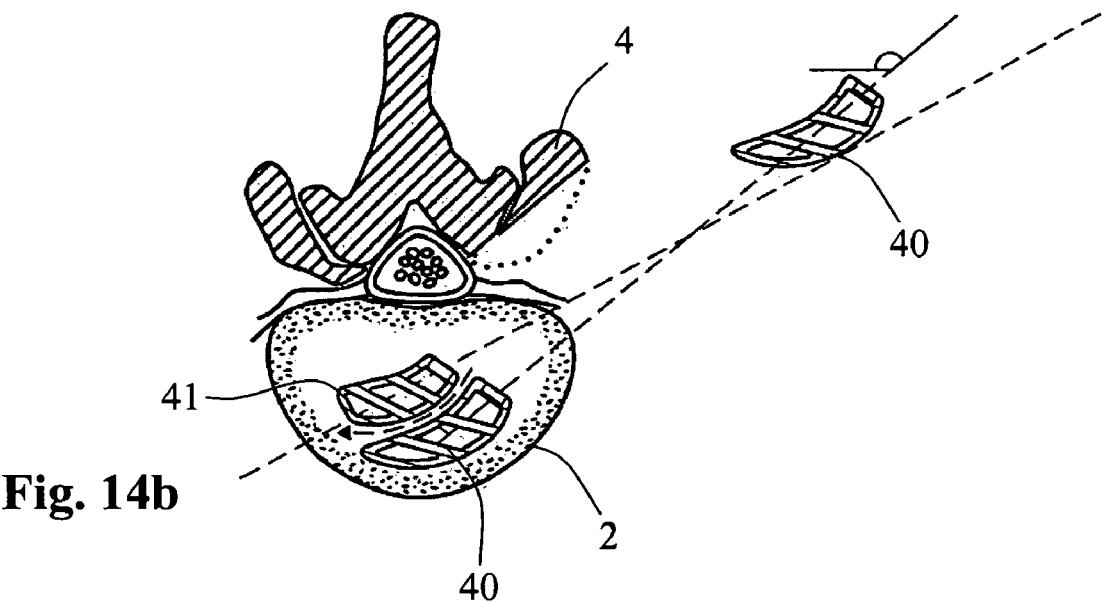
Figure 15:
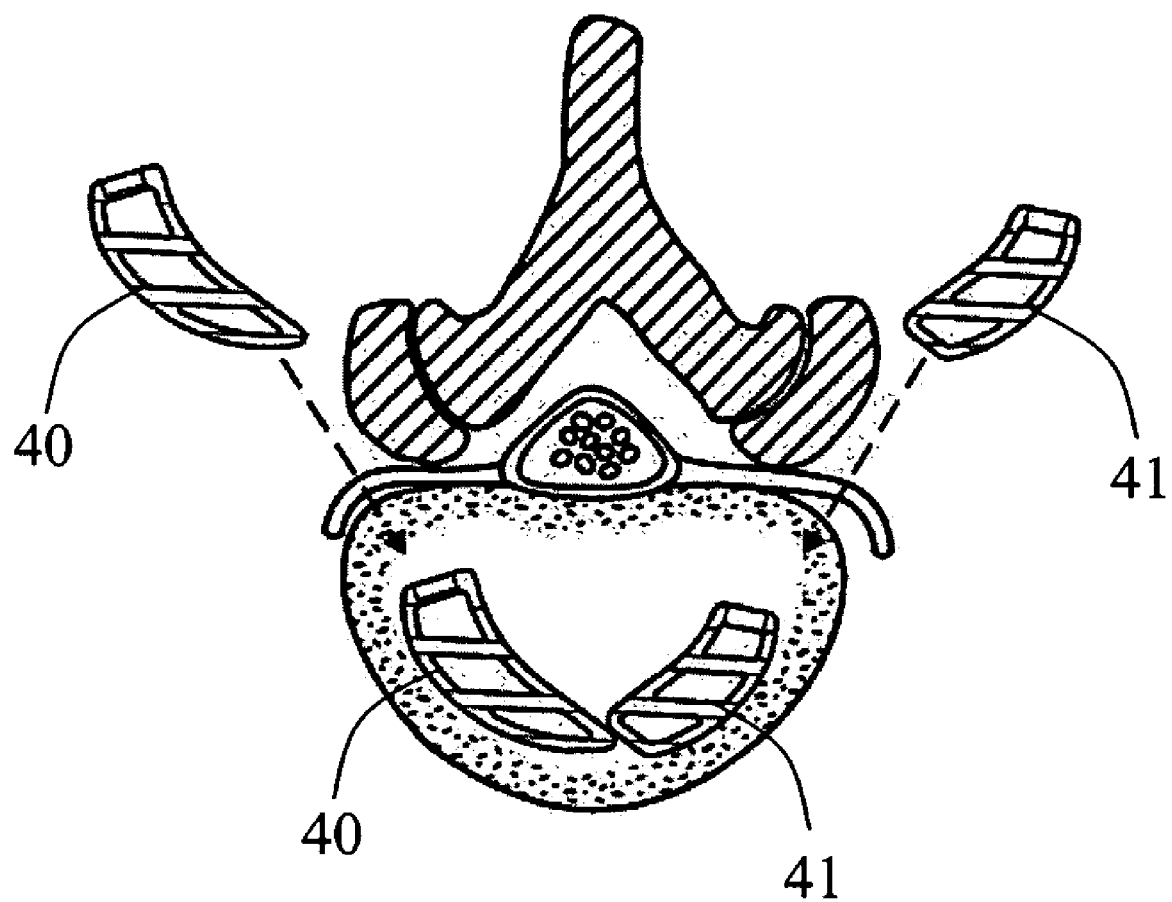

FIGS. 14a and 14b show a further show a further embodiment of the unilateral approach.

The first cage 40 is placed first more to the anterior of the interdisc space 24 and the second cage 41 more towards the anterior ring apophysis of the vertebral body.

FIG. 15 shows the unilateral approach. The first cage 40 is moved into the interdisc space 24 at a convergent 20° to 60° and preferably at about 30°. The cage 40 is specially designed to pass the midline and will contact and follow the natural curve of the annulus fibrosis at its insertion upon the ring apophysis. The far end of the cage 40 will mate with the second cage 41, which is inserted from a second incision in the contralateral side. The lordotic angle of angles of the cages 40 and 41 are suited for its placements and the convergent insertion at about 30°. Together both cages 40 and 41 form a wedge cylinder.

The cages 40 and 41 are illustrated in FIGS. 16 to 19 in detail. The preferred material for the cages 40 and 41 are from materials incorporating long carbon fibers where the fiber orientation is aligned according to the natural fibers of the bone trabecula of the bone structures that are designed to replace.

Both cages 40 and 41 have a hollow space which is filled with bone graft material (not shown). The surrounding vertebral endplate bone will grow into the graft material forming new bone tissue through the cage. The first cage 40 has an outer wall 66 with a curved outer surface 66 and a front wall 67 with a front surface 69. The wall 67 has a threaded opening 65 extending through the front wall 67 for receiving a threaded positioning tool (not shown). Two upwards struts 43 extend between the outer wall 66 and an inner wall. The struts 43 have two upper edge 70 and bottom edges 71 which are parallel to each other and which protrude on the upper side or bottom side of the cage 40. The struts 43 and edges 70 and 71 are aligned to prevent retropulsion and to keep the cage 40 seated in proper position.

Figure 16:
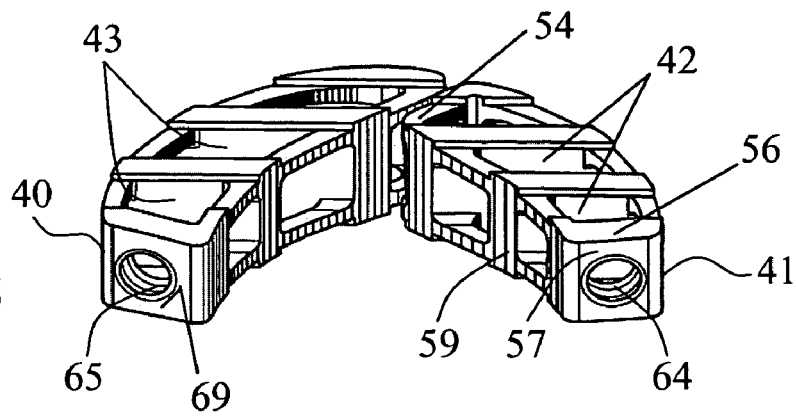
FIG. 16 is a perspective view of a preferred form of a pair of implants from the posterior view.
Figure 17:
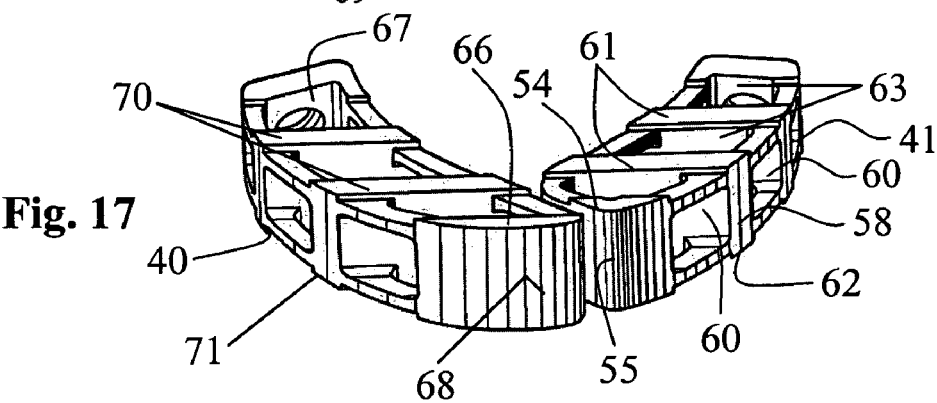
FIG. 17 is another view of the implants according to FIG. 16 from the anterior view.
Figure 18:
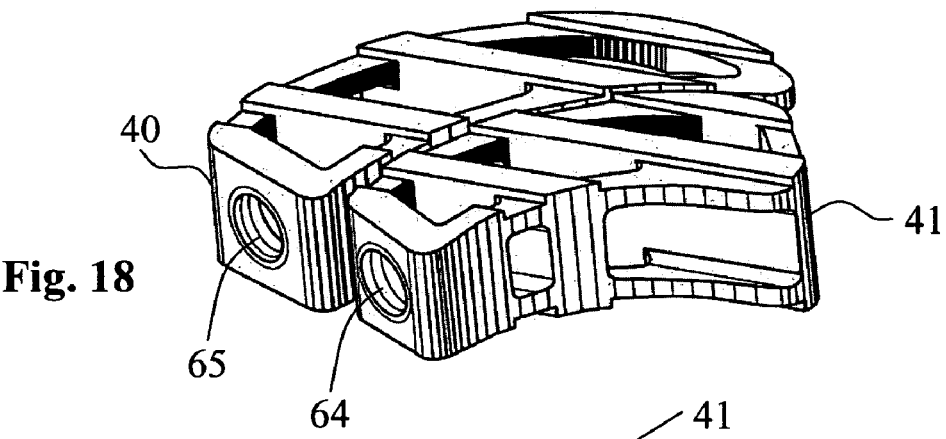
FIG. 18 is another arrangement and view of the implants according to FIG. 16 from the posterior view.
Figure 19:
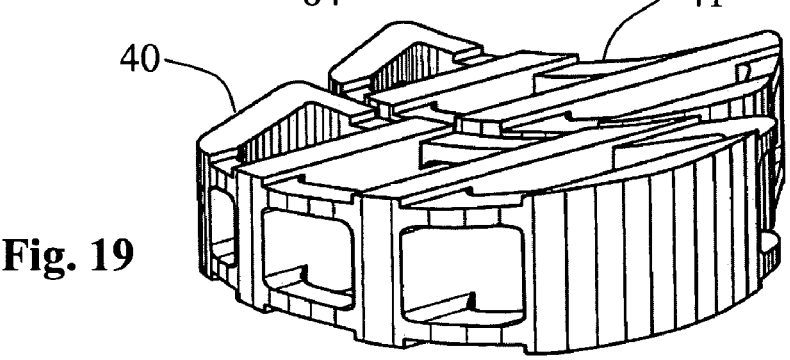
FIG. 19 is another view of the implants according to FIG. 18 from the anterior view.

The second cage 41 is shorter than the first cage 40 and has a front wall 54 with a front surface 55, that mates the first cage 40 as shown in FIGS. 16 and 17.

A rear wall 56 with a rear surface 57 has a threaded opening 64 extending through the wall for receiving a threaded positioning tool (not shown). An inner surface 59 and an outer surface 58 extend between the front wall 54 and the real wall 56 and are both curved. Openings 60 and 63 are in communication with a hollow space within the cage 41 which is filled with bone graft material. Two upward struts 42 extend between the outer surface 58 and the inner surface 59. The struts 42 have two top edges 61 and bottom edges 62 which are parallel to each other and which protrude at the upper side or bottom side of the cage 41. They are aligned to prevent retropulsion and to keep the cages 41 seated in proper position. The cages 40 and 41 can be arranged according to FIGS. 16 an 17 or according to FIGS. 18 and 19.

| REFERENCE NUMBERS | |
|---|---|
| 1 | spine |
| 2 | vertebra (L5) |
| 3 | endplate |
| 4 | superior articular process (L5) |
| 5 | inferior articular process (L4) |
| 6 | intertransverse ligament |
| 7 | Iliocostalis Lumborum pars Lumborum |
| 8 | Longissimus Thoracis pars Lumborum (LTPL) |
| 9 | Multifidus |
| 10 | Interfascial Boundary |
| 11 | Erector Spinae Aponeurosis (ESA) |
| 12 | ELIF Groove |
| 13 | fat |
| 14 | Thoracolumbar Fascia |
| 15 | fat |
| 16 | skin |
| 17 | incision |
| 18 | arrow showing the incision through skin and Thorical Lumbar Fascia |
| 19 | arrow showing the ELIF Lateral Trejctory Line |
| 20 | arrow showing path and incision along ELIF Groove to fin interfacial boundary |
| 21 | arrow showing ELIF trajectory into interfacial boundary |
| 22 | position (anatomical point of passage from posterior to anterior spine) |
| 23 | arrow ELIF trajectory line into disc space |
| 24 | interdisc space |
| 25 | arrow (incision) |
| 26 | — |
| 27 | arrow showing the retraction of skin, fat and Thoracis towards the midline |
| 28 | line |
| 29 | opening or ELIF surgical plane |
| 30 | arrow ELIF surgical trajectory |
| 31 | opening or ELIF surgical plane |
| 32 | arrow ELIF lateral trajectory into intertransverse ligament |
| 33 | arrow showing the retraction of the skin, fat and Thoracis fascia |
| 34 | arrow |
| 35 | screw |
| 36 | nut |
| 37 | threaded shaft |
| 38 | arrow ELIF lateral trajectory |

-continued

| REFERENCE NUMBERS | |
|---|---|
| 39 | arrow showing the cut into the intertransverse ligament |
| 40 | bilateral cage |
| 41 | bilateral cage |
| 42 | struts |
| 43 | struts |
| 44 | arrow showing the incision into skin, fat and Thorical Lumbar Fascia |
| 45 | line showing the level of L4-L5 |
| 46 | arrow showing the incision into skin, fat and Thorical Lumbar Fascia |
| 47 | arrow showing the incision along ELIF groove |
| 48 | arrow showing the incision along Illiac Crest |
| 49 | Erector Spinae Aponeurosis |
| 50 | sacrum |
| 51 | arrow showing the first cage entry along the ELIF lateral trajectory line |
| 52 | arrow showing the lateral translation of the first cage |
| 53 | arrow |
| 54 | front wall |
| 55 | front surface |
| 56 | rear wall |
| 57 | rear surface |
| 58 | outer surface |
| 59 | inner surface |
| 60 | side opening |
| 61 | top edge |
| 62 | bottom edge |
| 63 | opening |
| 64 | threaded opening |
| 65 | threaded opening |
| 66 | rear wall |
| 67 | front wall |
| 68 | rear surface |
| 69 | front surface |
| 70 | top edge |
| 71 | bottom edge |

The invention claimed is:

1. A method for repair of a spine from a posterior approach especially for locating an implant between a lower and upper human vertebra, comprising the steps of:
   a. making an incision in the skin lateral to the midline,
   b. making an incision through the Erector Spinae Aponeurosis (ESA) following an Extraforaminal Lumbar Interbody Fusion (ELIF) groove, wherein the ELIF groove appears as a valley in the ESA,
   c. separating the ESA from the Longissimus Thoracis Pars Lumborum (LTPL),
   d. atraumatic separating the Multifidus from the LTPL using the interfascial boundary between the Multifidus and the LTPL, and
   e. creating a surgical plane having an angle of 30°-60°.

2. The method of claim 1, wherein the inter-transverse ligament is opened where the superior aspect of the transverse process joins the lateral aspect of the superior articular process of the lumbar vertebra or where the sacral ala joins the lateral aspect of the superior articular facet of S1.

3. The method according to claim 1, wherein an interdisc space is entered at an angle of approximately 30°.

4. The method according to claim 1, wherein at least one cage is inserted between said lower and upper human vertebra.

5. The method according to claim 4, wherein a first and a second cage are inserted through the same opening.

6. The method according to claim 5, wherein the second cage pushes the first cage.

7. The method according to claim 1, including the step of: securing a stabilizing longitudinal device to the vertebrae above and below said first and second vertebrae to secure a distance between these vertebrae.

8. The method according to claim 1, comprising steps of:
   a. locating first and second cages, which carry bone or bone substitute material, between a lower and upper human vertebra having a space therebetween, wherein said vertebrae have dorsal processes extending posteriorly and each of said vertebrae have pedicle processes extending outwardly therefrom said vertebra being generally cylindrical having a porous core surrounded by an outer shell, said method comprising the steps of:
   b. inserting a cleaning tool sequentially through at least one opening at an angle sufficient to avoid the dorsal process;
   c. removing said tool;
   d. inserting cages through said opening toward the midline of said vertebrae so that said cages partially rest on and engage said outer shell,
   e. wherein a first cage being longer than a second cage and wherein these cages are not locked to each other,
   f. wherein the first and the second cage are inserted through the same opening in an extra-foraminal approach.

9. The method according to claim 8, wherein at least one of said cages is curved.

10. The method according to claim 1, wherein a facet prosthesis or an articular disc prosthesis is inserted between a lower and upper human vertebra.

11. The method according to claim 10, wherein the prosthesis is an articular disc prosthesis.

12. The method according to claim 1, wherein a facet joint is treated.

13. The method according to claim 12, wherein the facet joint is replaced.

14. Intervertebral implant for the method according to claim 1, wherein the implant comprises a pair of dissimilar cages.

15. Implant according to claim 14, wherein both cages are curved.

16. Implant according to claim 14, wherein the cages form a wedge cut out of a cylinder.

\* \* \* \* \*